United States Patent
Nakamura et al.

(10) Patent No.: US 10,799,116 B2
(45) Date of Patent: Oct. 13, 2020

(54) DEVICE AND METHOD OF MEASURING BLOOD FLOW

(71) Applicant: TOPCON CORPORATION, Itabashi-ku, Tokyo (JP)

(72) Inventors: Shunsuke Nakamura, Tokyo (JP); Jun Sakai, Kuki (JP)

(73) Assignee: TOPCON CORPORATION, Itabashi-ku, Tokyo (JP)

(*) Notice: Subject to any disclaimer, the term of this patent is extended or adjusted under 35 U.S.C. 154(b) by 345 days.

(21) Appl. No.: 15/754,157

(22) PCT Filed: Jul. 29, 2016

(86) PCT No.: PCT/JP2016/072436
§ 371 (c)(1),
(2) Date: Feb. 21, 2018

(87) PCT Pub. No.: WO2017/033671
PCT Pub. Date: Mar. 2, 2017

(65) Prior Publication Data
US 2018/0242845 A1    Aug. 30, 2018

(30) Foreign Application Priority Data
Aug. 26, 2015  (JP) ................................ 2015-166721

(51) Int. Cl.
*A61B 3/12*    (2006.01)
*A61B 3/10*    (2006.01)
(Continued)

(52) U.S. Cl.
CPC .......... *A61B 3/1233* (2013.01); *A61B 3/0025* (2013.01); *A61B 3/10* (2013.01);
(Continued)

(58) Field of Classification Search
CPC ............. G06T 2207/10101; G06T 7/74; G06T 2207/30104; G06T 2207/30041;
(Continued)

(56) References Cited

U.S. PATENT DOCUMENTS

2009/0005691 A1    1/2009   Huang et al.
2011/0267340 A1*  11/2011   Kraus .................... G06T 7/30
                                                            345/419
(Continued)

FOREIGN PATENT DOCUMENTS

JP    2009-165710 A    7/2009
JP    2010-523286 A    7/2010
(Continued)

OTHER PUBLICATIONS

International Search Report and Written Opinion dated Oct. 18, 2016, in connection with International Patent Application No. PCT/JP2016/072436, 8 pgs.

*Primary Examiner* — Pascal M Bui Pho
*Assistant Examiner* — Adil Partap S Virk
(74) *Attorney, Agent, or Firm* — Chiesa Shahinian & Giantomasi PC

(57) ABSTRACT

An embodiment is a blood flow measurement device that generates blood flow information based on data collected by repeatedly scanning an interested cross section intersecting a blood vessel of an eye fundus using OCT. A data collector scans four or more cross sections intersecting the blood vessel. A first calculator determines a first gradient and second gradient of the blood vessel by analyzing a first data group and second data group among four or more pieces of data corresponding to the four or more cross sections collected by the data collector. A second calculator determines a gradient of the blood vessel at the interested cross section based on the first gradient and the second gradient. A blood flow information generator generates the blood flow
(Continued)

information based on the gradient determined by the second calculator and the data collected by repeatedly scanning the interested cross section.

20 Claims, 10 Drawing Sheets

(51) Int. Cl.
| | |
|---|---|
| *A61B 5/00* | (2006.01) |
| *A61B 5/026* | (2006.01) |
| *G06T 7/73* | (2017.01) |
| *A61B 3/00* | (2006.01) |
| *A61B 3/14* | (2006.01) |
| *A61B 5/0285* | (2006.01) |

(52) U.S. Cl.
CPC ............... *A61B 3/102* (2013.01); *A61B 3/12* (2013.01); *A61B 3/1241* (2013.01); *A61B 3/14* (2013.01); *A61B 5/0066* (2013.01); *A61B 5/0261* (2013.01); *G06T 7/74* (2017.01); *A61B 5/0285* (2013.01); *G06T 2207/10101* (2013.01); *G06T 2207/30041* (2013.01); *G06T 2207/30104* (2013.01)

(58) Field of Classification Search
CPC ... A61B 3/1233; A61B 5/0261; A61B 5/0066; A61B 3/10; A61B 3/12; A61B 3/14; A61B 3/1241; A61B 3/102; A61B 3/0025; A61B 5/0285
See application file for complete search history.

(56) References Cited

U.S. PATENT DOCUMENTS

| | | | |
|---|---|---|---|
| 2015/0313466 A1* | 11/2015 | Yoshida | A61B 5/0066 600/425 |
| 2016/0302738 A1 | 10/2016 | Yoshida et al. | |
| 2016/0310024 A1 | 10/2016 | Yoshida et al. | |
| 2016/0317026 A1* | 11/2016 | Fingler | A61B 3/1005 |

FOREIGN PATENT DOCUMENTS

| | | | |
|---|---|---|---|
| JP | 2013-184018 A | 9/2013 | |
| JP | 2013-208158 A | 10/2013 | |
| WO | WO-2013137148 A1 * | 9/2013 | ............ G06T 11/60 |

* cited by examiner

FIG. 10

| | SUPPLEMENTARY CROSS SECTION | | | | GRADIENT | | |
|---|---|---|---|---|---|---|---|
| | C11 | C12 | C13 | C14 | θ1 | θ2 | θ |
| #1 | G11(1) | G12(1) | G13(1) | G14(1) | θ1(1) | θ2(1) | θ(1) |
| #2 | G11(2) | G12(2) | G13(1) | G14(1) | θ1(2) | θ2(2) | θ(2) |
| #3 | G11(2) | G12(2) | G13(2) | G14(2) | θ1(3) | θ2(3) | θ(3) |
| #4 | G11(3) | G12(3) | G13(2) | G14(2) | θ1(4) | θ2(4) | θ(4) |
| #5 | G11(3) | G12(3) | G13(3) | G14(3) | θ1(5) | θ2(5) | θ(5) |
| #6 | G11(4) | G12(4) | G13(3) | G14(3) | θ1(6) | θ2(6) | θ(6) |
| #7 | G11(4) | G12(4) | G13(4) | G14(4) | θ1(7) | θ2(7) | θ(7) |

DEVICE AND METHOD OF MEASURING BLOOD FLOW

CROSS-REFERENCE TO RELATED APPLICATIONS

This application is a national stage (under 35 U.S.C. 371) of International Patent Application No. PCT/JP2016/072436, filed Jul. 29, 2016, claiming priority to Japanese Patent Application No. 2015-166721, filed Aug. 26, 2015, both of which are herein incorporated by reference in their entirety.

FIELD

Embodiments described herein relate generally to a device and method for blood flow measurement.

BACKGROUND

Optical coherence tomography (OCT) is utilized not only for morphology measurement of an object but also for function measurement. For example, OCT apparatuses for blood flow measurement of living bodies are known. The blood flow measurement using OCT is applied to blood vessels of the eye fundus.
[Patent Document 1] Japanese Unexamined Patent Application Publication No. 2013-184018
[Patent Document 2] Japanese Unexamined Patent Application Publication No. 2009-165710
[Patent Document 3] Japanese Unexamined Patent Application Publication (Translation of PCT Application) No. 2010-523286

In general, the acquisition of the blood flow information using OCT requires the estimation of the orientation of the blood vessel to be measured. This is because the blood flow information is determined based on the Doppler frequency shift that varies according to the angle between the blood flow direction (i.e., the orientation of the blood vessel) and the incident direction of the measurement light on the blood vessel.

In the conventional eye fundus blood flow measurement, a cross section (i.e., a supplementary cross section) is set on the upstream side and the downstream side of the blood vessel with respect to a cross section to be measured (i.e., an interested cross section). The orientation of blood vessel is estimated from the cross sectional images of these supplementary cross sections. In such a method, the distance between the two supplementary cross sections and the distance of the supplementary cross sections to the interested cross section influence the estimation result. Specifically, the distance between the supplementary cross sections influences the accuracy and precision of the estimation, and the larger this distance, the better. On the other hand, the distance of the supplementary cross sections to the interested cross section influences the error caused by meandering of the blood vessel, and the smaller this distance, the better. Thus, these two factors are in a trade-off relationship to each other. In the conventional typical technique, supplementary cross sections are set at positions 100 µm away from the interested cross section on the upstream side and the downstream side. That is, typically the distance between the supplementary cross sections is 200 µm and the distance of the supplementary cross section to the interested cross section is 100 µm.

SUMMARY

A purpose of the blood flow measurement device and the blood flow measurement method according to the present embodiment is to optimize setting of the supplementary cross sections for estimating the orientation of the blood vessel.

An embodiment is a blood flow measurement device that generates blood flow information based on data collected by repeatedly scanning an interested cross section intersecting a blood vessel of an eye fundus using optical coherence tomography. The blood flow measurement device includes a data collector, a first calculator, a second calculator, and a blood flow information generator. The data collector collects data by scanning four or more cross sections intersecting the blood vessel using optical coherence tomography. The first calculator determines a first gradient of the blood vessel by analyzing a first data group consisting of two or more pieces of data among four or more pieces of data corresponding to the four or more cross sections collected by the data collector and that determines a second gradient of the blood vessel by analyzing a second data group consisting of two or more pieces of data including one or more pieces of data that is not included in the first data group. The second calculator determines a gradient of the blood vessel at the interested cross section based on the first gradient and the second gradient determined by the first calculator. The blood flow information generator generates the blood flow information based on the gradient determined by the second calculator and the data collected by repeatedly scanning the interested cross section.

According to the embodiment, setting of the supplementary cross sections for estimating the orientation of the blood vessel can be optimized.

BRIEF DESCRIPTION OF THE DRAWINGS

FIG. 10 is a schematic diagram for describing an example of the operation of the blood flow measurement device according to the embodiment.

DETAILED DESCRIPTION

Figure 1:
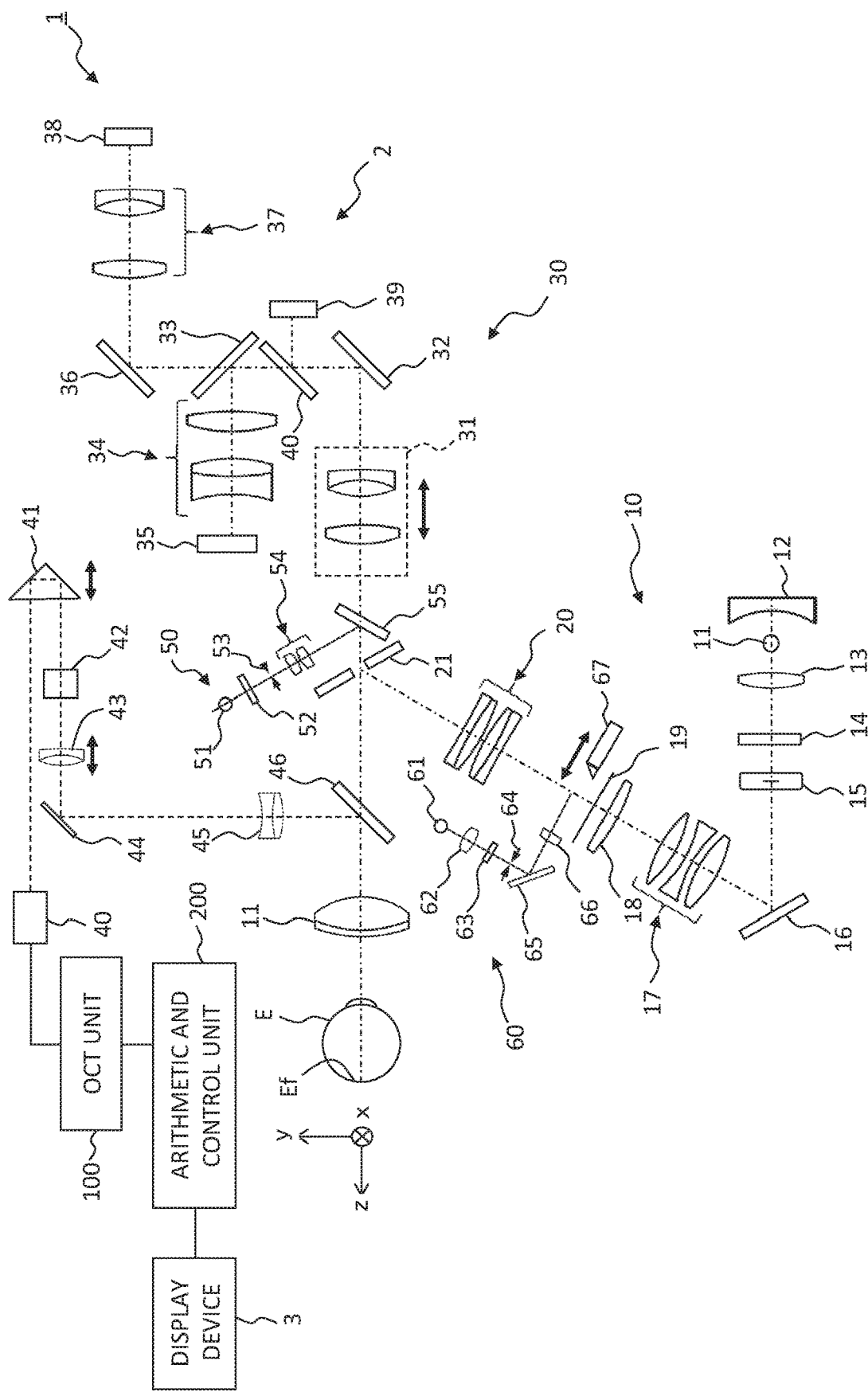
FIG. 1 is a schematic diagram illustrating an example of the configuration of the blood flow measurement device according to the embodiment.

A blood flow measurement device according to an embodiment will be described in detail with referring to the drawings. The blood flow measurement device according to the embodiment forms a cross sectional image and a three dimensional image of an eye of a living body using the OCT. The contents of the cited documents described in the present specification may be applied to embodiments.

In the following embodiments, a blood flow measurement device that performs OCT on the eye fundus using Fourier domain OCT (in particular, spectral domain OCT) will be described. Note that the type of the OCT is not limited to the spectral domain OCT. A type of OCT such as swept source OCT may be utilized. The blood flow measurement device according to the embodiment is a multifunctional device that is a combination of an OCT apparatus and a fundus camera. However, the blood flow measurement device may be a combination of an OCT apparatus and an eye fundus photographing apparatus other than a fundus camera. The eye fundus photographing apparatus is, for example, a scanning laser ophthalmoscope (SLO), a slit lamp microscope, or an ophthalmic operation microscope. Note that the blood flow measurement device is sufficient as long as it has the OCT function, and having the fundus photographing function is not necessary.

[Configuration]

As shown in FIG. 1, the blood flow measurement device 1 includes the fundus camera unit 2, the OCT unit 100, and the arithmetic and control unit 200. The fundus camera unit 2 has substantially the same optical system as the conventional fundus camera. The OCT unit 100 includes an optical system for acquiring OCT images of the eye fundus. The arithmetic and control unit 200 includes a computer that performs various arithmetic processes and control processes.

(Fundus Camera Unit 2)

As illustrated in FIG. 1, the fundus camera unit 2 is provided with an optical system for acquiring two dimensional images (i.e., fundus images) rendering the surface morphology of the fundus Ef of the subject's eye E. Examples of the fundus images include observation images and photographed images. An observation image is, for example, a monochrome moving image formed at a predetermined frame rate using near-infrared light. A photographed image is, for example, a color image captured by flashing visible light, or a monochrome still image captured using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. In addition, the fundus camera unit 2 is provided with the illumination optical system 10 and the photographing optical system 30. The illumination optical system 10 projects illumination light onto the fundus Ef. The photographing optical system 30 guides the illumination light reflected from the fundus Ef to an imaging device (i.e., the CCD image sensor 35 or 38). Each of the CCD image sensors 35 and 38 is sometimes simply referred to as "CCD". Further, the photographing optical system 30 guides measurement light coming from the OCT unit 100 to the fundus Ef, and guides the measurement light returning from the fundus Ef to the OCT unit 100.

The observation light source 11 of the illumination optical system 10 includes, for example, a halogen lamp or a light emitting diode (LED). The light output from the observation light source 11 (i.e., observation illumination light) is reflected by the reflection mirror 12 having a concave reflective surface, passes through the condenser lens 13, and becomes near-infrared light after passing through the visible cut filter 14. Further, the observation illumination light is once converged near the photographing light source 15, reflected by the mirror 16, and passes through the relay lenses 17 and 18, the diaphragm 19, and the relay lens 20. Then, the observation illumination light is reflected on the peripheral part (i.e., the surrounding area of the aperture part) of the aperture mirror 21, penetrates the dichroic mirror 46, and refracted by the objective lens 22, thereby illuminating the fundus Ef.

The observation illumination light reflected from the fundus Ef is refracted by the objective lens 22, penetrates the dichroic mirror 46, passes through the aperture part formed in the center area of the aperture mirror 21, passes through the dichroic mirror 55, travels through the focusing lens 31, and is reflected by the mirror 32. Further, the fundus reflection light passes through the half mirror 40, is reflected by the dichroic mirror 33, and forms an image on the light receiving surface of the CCD image sensor 35 by the condenser lens 34. The CCD image sensor 35 detects the fundus reflection light at a predetermined frame rate. An image based on the fundus reflection light detected by the CCD image sensor 35 (i.e., observation image) is displayed on the display device 3. Note that when the focus of the photographing optical system 30 is adjusted to the anterior segment of the subject's eye E, an observation image of the anterior segment of the subject's eye E is acquired and displayed.

The photographing light source 15 includes, for example, a xenon lamp or an LED. The light output from the photographing light source 15 (i.e., photographing illumination light) is guided to the fundus Ef along the same route as that of the observation illumination light. The photographing illumination light reflected from the fundus Ef is guided to the dichroic mirror 33 along the same route as that of the observation illumination light, passes through the dichroic mirror 33, is reflected by the mirror 36, and forms an image on the light receiving surface of the CCD image sensor 38 by the condenser lens 37. The display device 3 displays an image based on the fundus reflection light detected by the CCD image sensor 38 (i.e., photographed image).

The liquid crystal display (LCD) 39 displays a fixation target and a visual target used for visual acuity measurement. The fixation target is a visual target for fixating the subject's eye E, and is used when performing fundus photography and OCT measurement. By changing the display position of the fixation target on the screen of the LCD 39, the fixation position of the subject's eye E can be changed.

Part of the light output from the LCD 39 is reflected by the half mirror 33A, reflected by the mirror 32, travels through the focusing lens 31 and the dichroic mirror 55, and passes through the aperture part of the aperture mirror 21. The light passed through the aperture part of the aperture mirror 21 penetrates the dichroic mirror 46, and is refracted by the objective lens 22, thereby being projected onto the fundus Ef.

In addition, as with a conventional fundus camera, the fundus camera unit 2 is provided with the alignment optical system 50 and the focus optical system 60. The alignment optical system 50 generates an indicator (i.e., an alignment indicator) for the position adjustment (i.e., the alignment) of the optical system with respect to the subject's eye E. The focus optical system 60 generates an indicator (i.e., a split indicator) for adjusting the focus with respect to the fundus Ef.

The light output from the LED 51 of the alignment optical system 50 (i.e., alignment light) travels through the diaphragms 52 and 53 and the relay lens 54, is reflected by the dichroic mirror 55, and passes through the aperture part of the aperture mirror 21. The alignment light then penetrates the dichroic mirror 46, and is projected onto the subject's eye E by the objective lens 22.

The returning light of the alignment light is detected by the CCD image sensor 35. The received image captured by the CCD image sensor 35 (i.e., alignment indicator image) is displayed together with the observation image. As with the conventional fundus camera, the user can perform alignment while referring to the alignment indicator image. Instead, alignment may be performed in such a way that the arithmetic and control unit 200 analyzes the position of the alignment indicator image and moves the optical system (automatic alignment).

To conduct focus adjustment, the reflective surface of the reflection rod 67 is arranged in a slanted position on the optical path of the illumination optical system 10. The light output from the LED 61 of the focus optical system 60 (i.e., focus light) passes through the relay lens 62, is split into two light beams by the split indicator plate 63, passes through the two-hole diaphragm 64. The light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, penetrates the dichroic mirror 46, and is refracted by the objective lens 22, thereby being projected onto the fundus Ef.

The returning light of the focus light is detected by the CCD image sensor 35. The received image captured by the CCD image sensor 35 (i.e., split indicator image) is displayed together with the observation image and the alignment indicator image. As in the conventional case, the arithmetic and control unit 200 can analyze the position of the split indicator image, and move the focusing lens 31 and the focus optical system 60 for the focus adjustment (automatic focusing). Instead, the user may manually perform the focus adjustment while referring to the position of the split indicator image.

The dichroic mirror 4 superposes the optical path for OCT (OCT optical path) on the optical path for fundus photography. That is, the optical path for fundus photography and the OCT optical path are arranged coaxially through the dichroic mirror 46, and share the optical path on the subject's eye E side with respect to the dichroic mirror 46. The dichroic mirror 46 reflects light of wavelengths used in OCT, and transmits light for fundus photography. The OCT optical path is provided with, in order from the OCT unit 100 side, the collimator lens unit 40, the optical path length (OPL) changer 41, the galvano scanner 42, the focusing lens 43, the mirror 44, and the relay lens 45.

The optical path length changer 41 is movable in directions indicated by the arrow in FIG. 1 to change the length of the OCT optical path. The change in the optical path length is used for correcting the optical path length according to the axial length of the subject's eye E, for adjusting the interference state, and the like. The optical path length changer 41 includes, for example, a corner cube and a mechanism for moving the corner cube.

The galvano scanner 42 changes the traveling direction of the measurement light LS that travels along the OCT optical path. With this, the fundus Ef can be scanned with the measurement light LS. The galvano scanner 42 includes, for example, a galvano mirror that deflects the measurement light LS in the x direction, a galvano mirror that deflects the measurement light LS in the y direction, and a mechanism(s) that independently drives the galvano mirrors. With this, it is possible to scan the measurement light LS in an arbitrary direction in the xy plane.

(OCT Unit 100)

Figure 2:
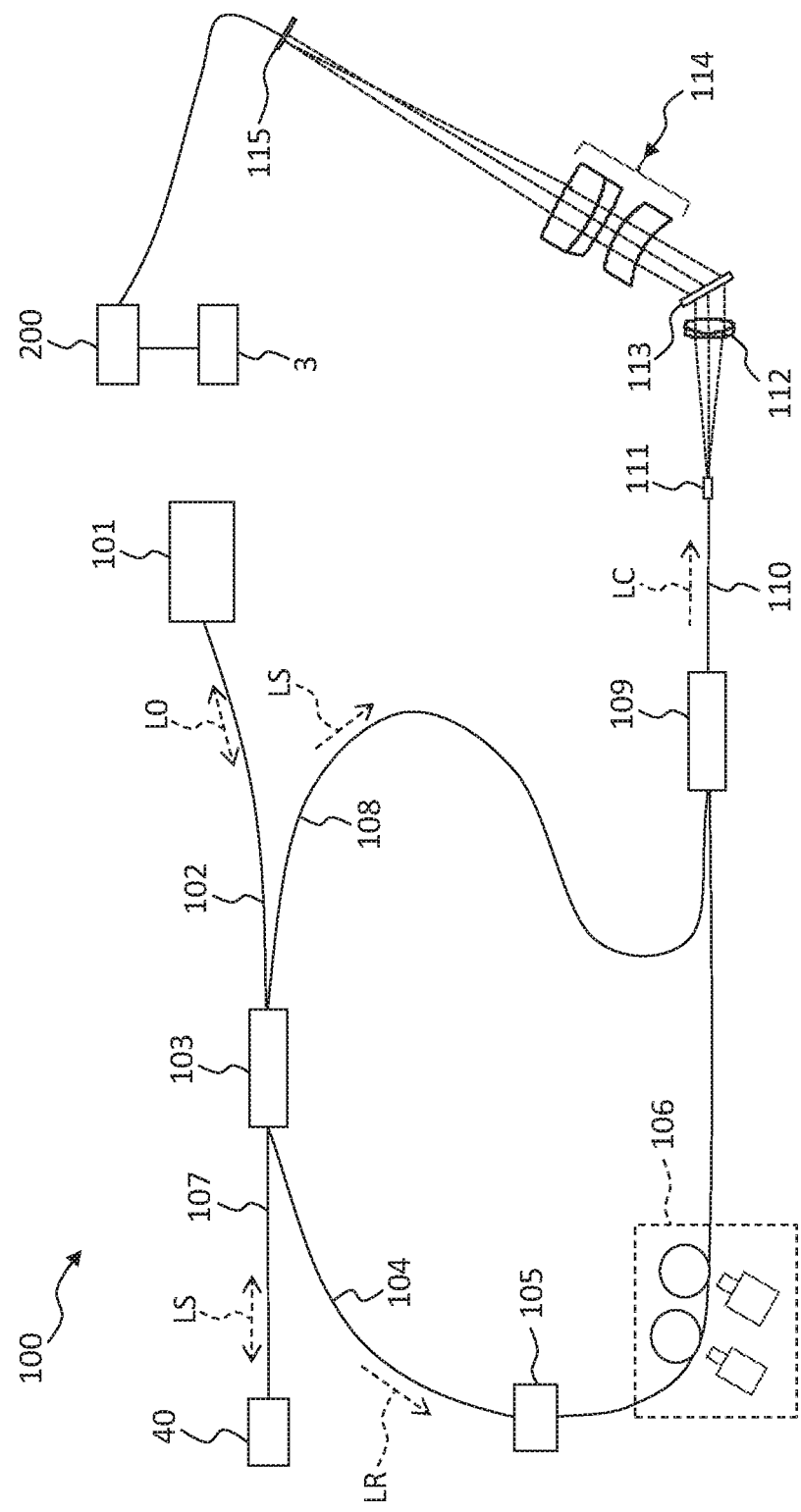
FIG. 2 is a schematic diagram illustrating an example of the configuration of the blood flow measurement device according to the embodiment.

An exemplary configuration of the OCT unit 100 will be described with referring to FIG. 2. The OCT unit 100 includes an optical system for acquiring OCT images of the fundus Ef. As with the conventional spectral domain OCT apparatus, this optical system is configured to split the low coherence light into reference light and measurement light, superpose the measurement light having traveled through the fundus Ef and the reference light having traveled through the reference optical path to generate interference light, and detect spectral components of the interference light. The detection result (i.e., detection signal) is sent to the arithmetic and control unit 200.

When a swept source OCT apparatus is employed, a wavelength tunable light source is provided instead of a low coherence light source, and a balanced photodiode is provided instead of a device for detecting a spectral component(s) (i.e., spectrometer). In general, the OCT unit 100 may have a known configuration according to the type of OCT.

The light source unit 101 outputs the low coherence light L0 (broadband light). The low coherence light L0, for example, includes a wavelength band (e.g., about 800 nm to 900 nm) in the near-infrared region and has a temporal coherence length of about several tens of micrometers. Alternatively, the low coherence light L0 may be near-infrared light having the central wavelength of 1040 nm to 1060 nm.

The light source unit 101 includes a light emitting device such as a super luminescent diode (SLD), an LED, or a semiconductor optical amplifier (SOA).

The low coherence light L0 output from the light source unit 101 is guided to the fiber coupler 103 through the optical fiber 102, and is split into the measurement light LS and the reference light LR.

The reference light LR is guided to the optical attenuator 105 through the optical fiber 104. Under the control of the arithmetic and control unit 200 or by manual operation, the optical attenuator 105 adjusts the light amount of the reference light LR guided through the optical fiber 104. The reference light LR, the light amount of which has been adjusted by the optical attenuator 105, is guided to the polarization controller 106 through the optical fiber 104. The polarization controller 106 changes the polarization state of the reference light LR guided through the optical fiber 104. The reference light LR, the polarization state of which has been adjusted by the polarization controller 106, is guided to the fiber coupler 109.

The measurement light LS generated by the fiber coupler 103 is guided through the optical fiber 107, and is converted to a parallel light beam with the collimator lens unit 105. Then, the measurement light LS passes through the optical path length changer 41, the galvano scanner 42, the focusing lens 43, the mirror 44, and the relay lens 45, and reaches the dichroic mirror 46. Further, the measurement light LS is reflected by the dichroic mirror 46, is refracted by the objective lens 11, and is incident on the subject's eye E. The measurement light LS is reflected and scattered at various depth positions of the fundus Ef. Returning light of the measurement light LS from the fundus Ef (e.g., backscattering light, reflection light, fluorescence) travels along the same route as the outward way in the opposite direction, is guided to the fiber coupler 103, and is guided to the fiber coupler 109 through the optical fiber 108.

The fiber coupler 109 superposes the returning light of the measurement light LS and the reference light LR. With this, the interference light LC is generated. The interference light LC is guided through the optical fiber 110, and exits from the exit end 111 of the optical fiber 110. Then, the interference light LC is converted to a parallel light beam with the collimator lens 112, is split into spectra with the diffraction grating 113, converges with the condenser lens 114, and is projected on the light receiving surface of the CCD image sensor 115. Note that although FIG. 2 illustrates the diffraction grating 113 of a transmission type, it is also possible to use a spectrally decomposing element of any other type, such as a diffraction grating of reflection type.

The CCD image sensor 115 is, for example, a line sensor, and detects the spectral components of the interference light LC and converts the components into electric charges. The CCD image sensor 115 accumulates the electric charges to generate a detection signal, and sends the signal to the arithmetic and control unit 200. Instead of the CCD image sensor, another kind of image sensor, such as a complementary metal oxide semiconductor (CMOS) image sensor, may be provided.

(Arithmetic and Control Unit 200)

The arithmetic and control unit 200 analyzes the detection signals input from the CCD image sensor 115 to form an OCT image of the fundus Ef. The arithmetic processing for forming OCT images of the fundus Ef is the same as the conventional spectral domain OCT.

In addition, the arithmetic and control unit 200 controls the fundus camera unit 2, the display device 3 and the OCT unit 100. The control of the fundus camera unit 2 includes the operation control of the observation light source 11, the photographing light source 15, the LCD 39, the galvano scanner 42, and the LEDs 51 and 61. The control of the fundus camera unit 2 also includes the movement control of the focusing lenses 31 and 43, the optical path length changer 41, the focus optical system 60, and the reflection rod 67. The control of the OCT unit 100 includes the operations control of the light source unit 101, the optical attenuator 105, the polarization controller 106, and the CCD image sensor 120.

The arithmetic and control unit 200 includes a processor, a RAM, a ROM, a hard disk drive, a communication interface, and the like. In addition, the arithmetic and control unit 200 may include an operation device (input device) such as a keyboard and a mouse, and a display device such as an LCD. In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The arithmetic and control unit 200 realizes the functions according to the embodiment, for example, by reading out and executing a program stored in a storage circuit or a storage device.

[Control System]

Figure 3:
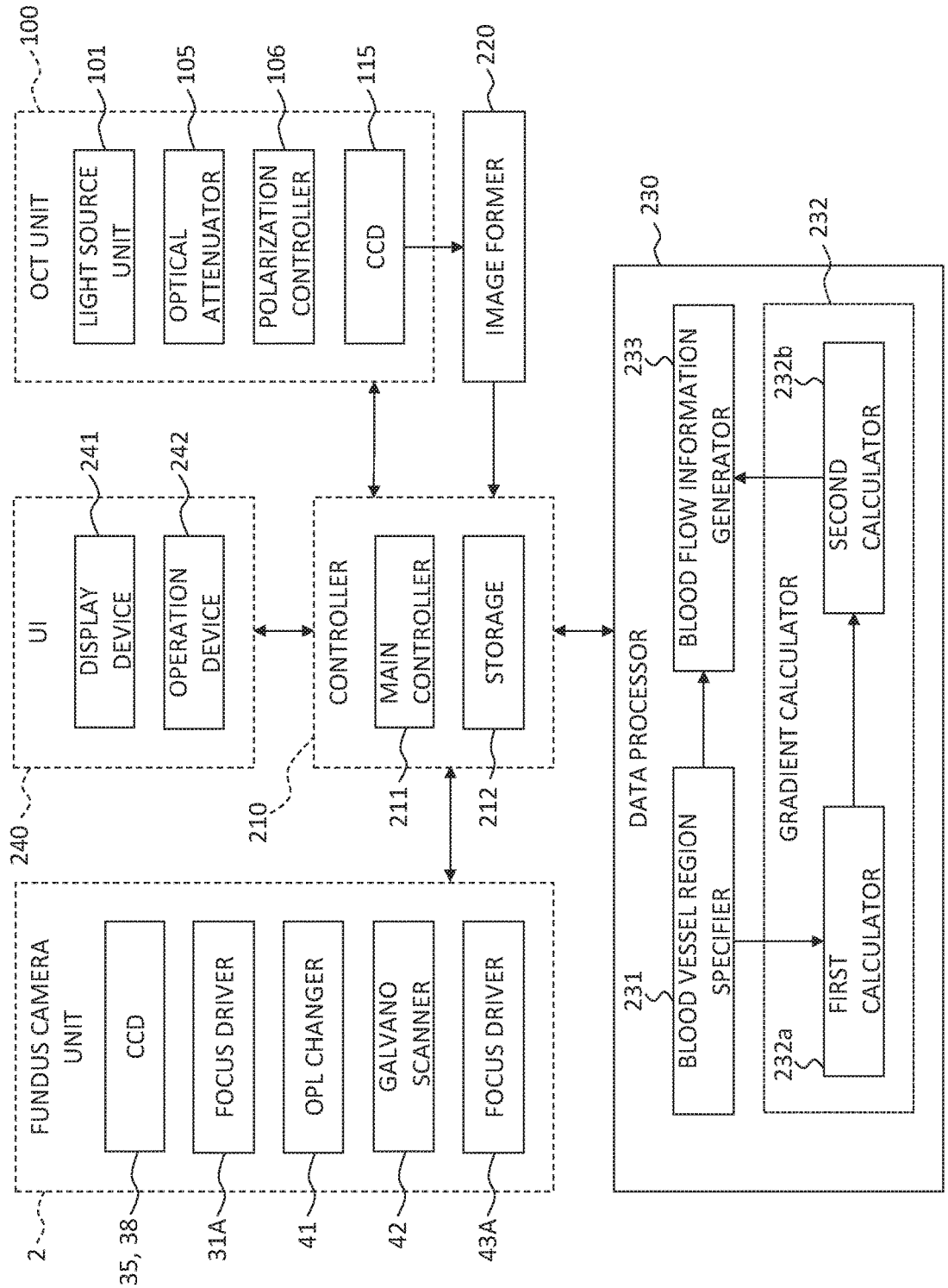
FIG. 3 is a schematic diagram illustrating an example of the configuration of the blood flow measurement device according to the embodiment.
Figure 4:
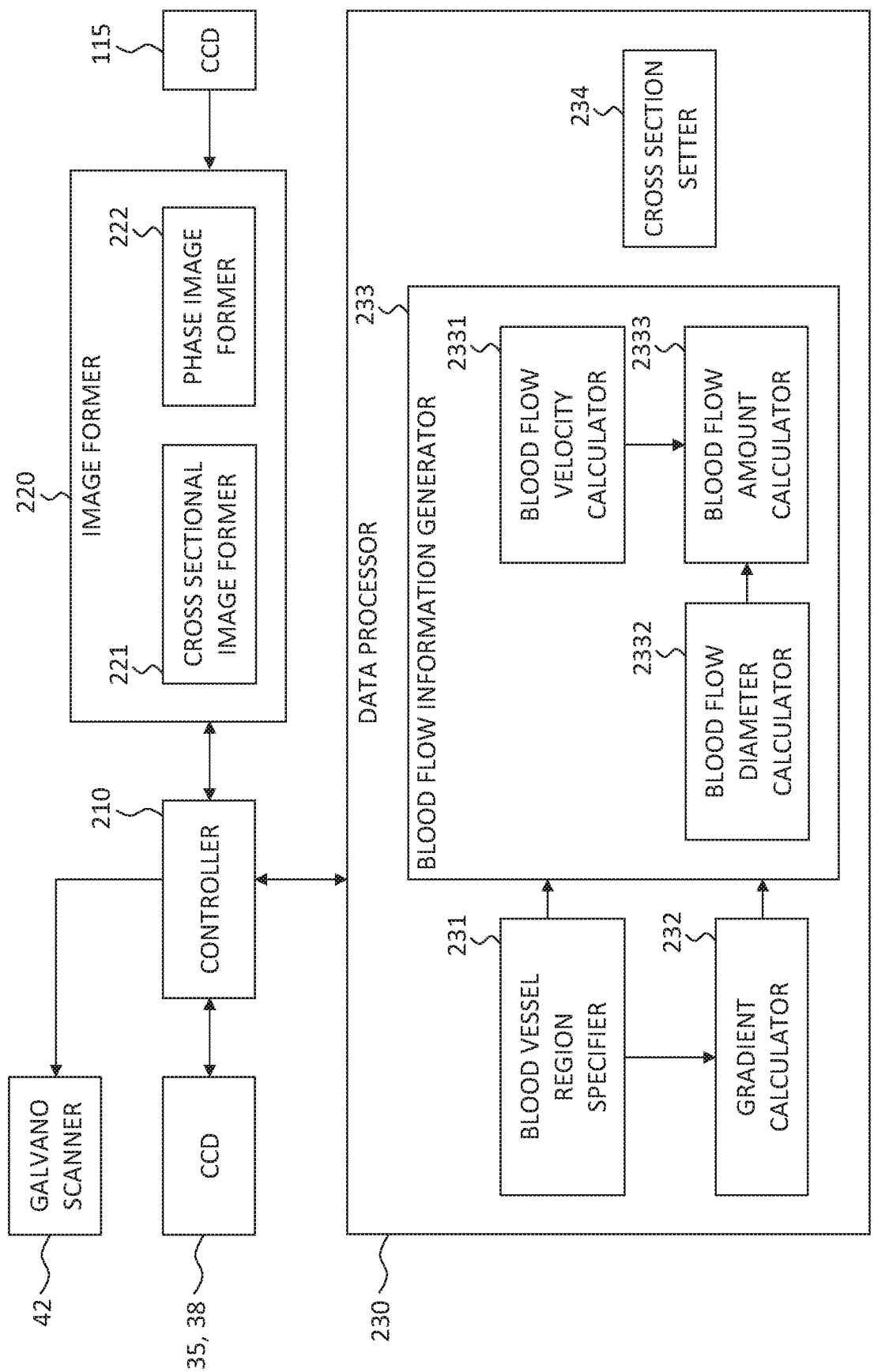
FIG. 4 is a schematic diagram illustrating an example of the configuration of the blood flow measurement device according to the embodiment.

The configuration of the control system of the blood flow measurement device 1 will be described with referring to FIGS. 3 and 4.

(Controller 210)

The controller 210 includes, for example, the aforementioned processor, RAM, ROM, hard disk drive, communication interface, and the like. The controller 210 is provided with the main controller 211 and the storage 212. The storage 212 stores various kinds of data and computer programs.

The main controller 211 executes various controls. For example, as shown in FIG. 3, the main controller 211 executes controls of the CCDs 35 and 38, the focus driver 31A, the optical path length changer 41, the galvano scanner 42, and the focus driver 43A of the fundus camera unit 2. Further, the main controller 211 controls the light source unit 101, the optical attenuator 105, the polarization controller 106, and the CCD 115 of the OCT unit 100.

The focus driver 31A moves the focusing lens 31 in the optical axis direction. As a result, the focal position of the photographing optical system 30 changes. Further, the focus driver 43A moves the focusing lens 43 in the optical axis direction. As a result, the focal position of the measurement light LS (i.e., focal position for OCT measurement) changes. The main controller 211 can control an optical system driver (not illustrated) to move the optical system of the fundus camera unit 2 in the three dimensional manner. This movement control of the optical system is used in alignment and tracking. Here, tracking is a process of moving the optical system of the blood flow measurement device 1 according to the movement of the subject's eye E. Alignment and focus adjustment are performed before tracking. Tracking is a function to maintain a suitable alignment state and a suitable focus state by making the position of the optical system follow eye movement.

(Image Former 220)

The image former 220 forms image data of a cross sectional image of the fundus Ef and image data of a phase image of the fundus Ef based on detection signals from the CCD image sensor 115. The image former 220 includes a processor. In the present specification, "image data" and an "image" based thereon may not be distinguished from each other. The image former 220 has the cross sectional image former 221 and the phase image former 222.

In the present embodiment, two types of scans (i.e., first scan and second scan) are executed on the fundus Ef. In the first scan, four or more cross sections (supplementary cross sections) intersecting an interested blood vessel of the fundus Ef are scanned with the measurement light LS. I the second scan, an interested cross section intersecting the interested blood vessel is repetitively scanned with the measurement light LS. The supplementary cross sections on which the first scan is executed are set near the interested cross section. The data acquired through the first scan is used to determine the orientation (i.e., gradient, or inclination angle) of the interested blood vessel at the interested cross section. The second scan is Doppler measurement using OCT.

It may be desirable that the cross sections to be scanned in the first scan and the cross section to be scanned in the second scan are oriented, in the xy plane, in such a manner that they are orthogonal to the running direction of the interested blood vessel. As shown in the fundus image D of FIG. 5, in the present embodiment, for example, the four supplementary cross sections C11 to C14 where the first scan is to be executed and the interested cross section C2 where the second scan is to be executed are set, in the vicinity of the optic nerve head Da, to intersect with the interested blood vessel Db.

Two of the four supplementary cross sections C11 to C14 (for example, the supplementary cross sections C11 and C12) are located on the upstream side of the interested blood vessel Db with respect to the interested cross section C2, and the other two (for example, the supplementary cross sections C13 and C14) are located on the downstream side. The supplementary cross sections C12 and C13 are disposed adjacent to the interested cross section C2. The supplementary cross section C11 is disposed on the opposite side of the interested cross section C2 with respect to the supplementary cross section C12, and the supplementary cross section C14 is disposed on the opposite side of the interested cross section C2 with respect to the supplementary cross section C13. In other words, the supplementary cross section C11 is disposed on the most upstream side, and the supplementary cross section C14 is disposed on the most downstream side.

The distance of each of the supplementary cross section C12 and C13 to the interested cross section C2 is set in advance. Also, the distance between the supplementary cross section C11 and the supplementary cross section C12, and the distance between the supplementary cross section C13 and the supplementary cross section C14 are set in advance. In the present example, five cross sections consisting of the supplementary cross sections C11 to C14 and the interested cross section C2 are equally spaced. The interval between these five cross sections is set to a value within the range of 50 μm to 100 μm, for example. In this case, the distance between the supplementary cross sections C11 and C14 located at both ends is within the range of 200 μm to 400 μm.

The number of supplementary cross sections is not limited to four, and may be five or more. The interval of N+1 cross sections including N (N≥4) supplementary cross sections and an interested cross section (referred to as cross section interval) is arbitrarily set, and the distance between the cross sections located at both ends of these cross sections (referred to as cross section overall width) is arbitrarily set. The cross section interval influences the error caused by meandering of the blood vessel. The smaller the cross section interval is set, the smaller the error becomes. On the other hand, the cross section overall width influences the accuracy and precision of gradient calculation of the interested blood vessel. The larger the cross section overall width is set, the higher the accuracy and precision of the calculation becomes. When the number of the supplementary cross sections is an even number as in the present example, the interested cross section can be disposed at the center of the odd number of cross sections including the interested cross section.

Also, the number of the supplementary cross sections can be arbitrarily set. If the number of the supplementary cross sections is increased, the error caused by meandering of the blood vessel can be reduced. In this case, however, since the scanning period is prolonged, the influence of the error caused by the movement of the subject's eye E increases. According to the present example, conditions of the first scan can be set while individually or comprehensively considering the above factors.

It may be desirable that the second scan is executed during a period equal to or longer than one heartbeat (i.e., one pulsation cycle, or cardiac cycle) of the heart of the patient. With this, blood flow information is acquired for all time phases of the cardiac cycle. The execution period of the second scan may be a preset period with a constant length, or may be set for each patient or each examination.

(Cross Sectional Image Former 221)

The cross sectional image former 221 forms cross sectional images corresponding to the respective supplementary cross sections C11 to C14 based on the detection results of the interference light LC acquired through the first scan on the four supplementary cross sections C11 to C14. At this time, each of the supplementary cross sections C11 to C14 may be scanned once and a single cross sectional image may be formed for each of the supplementary cross sections C11 to C14. Alternatively, each of the supplementary cross sections C11 to C14 may be scanned a plurality of times, and a plurality of cross sectional images may be formed for each of the supplementary cross sections C11 to C14.

The cross sectional image former 221 forms a cross sectional image group that represents the time-dependent change in morphology in the interested cross section C2 based on the detection results of the interference light LC acquired through the second scan on the interested cross section C2. This image formation will be described in more detail. In the second scan, the interested cross section C2 is repeatedly scanned as described above. During the second scan, detection signals are successively transmitted from the CCD 115 of the OCT unit 100 to the cross sectional image former 221. Based on the detection signal group corresponding to a single scan of the interested cross section C2, the cross sectional image former 221 forms a single cross sectional image of the interested cross section C2. The cross sectional image former 221 repeats such image formation as many times as the number of repetition of the second scan, thereby forming a series of cross sectional images arranged in time series order. The cross sectional image former 221 may divide these cross sectional images into a plurality of groups and averages cross sectional images in each group to improve image quality.

Processing executed by the cross sectional image former 221 includes noise elimination (noise reduction), filtering, fast Fourier transform (FFT), and the like as in conventional spectral domain OCT techniques. When other type of OCT is applied, the cross sectional image former 221 executes known processing according to the type of OCT.

(Phase Image Former 222)

The phase image former 222 forms a phase image that represents the time-dependent change in phase difference in the interested cross section C2 based on detection results of the interference light LC acquired through the second scan on the interested cross section C2. The data processed here is the same as that processed in the formation of the cross sectional image of the interested cross section C2 performed by the cross sectional image former 221. Accordingly, position matching between the phase image and the cross sectional image of the interested cross section C2 can be performed. That is, pixels in the cross sectional image of the interested cross section C2 and those in the phase image can be associated with each other in a natural manner.

An example of the method of the formation of phase images will be described. A phase image in the present example is obtained by calculating the phase differences between adjacent A-line complex signals (that is, signals corresponding to adjacent scan points). In other words, a phase image in the present is formed based on time-dependent change in the pixel value (brightness value) of each pixel in the cross sectional image of the interested cross section C2. For any pixel, the phase image former 222 takes account of a graph representing the time-dependent change in the brightness value of the concerned pixel. The phase image former 222 determines the phase difference $\Delta \varphi$ between two time points t1 and t2 that are apart from each other by a preset time interval $\Delta t$ in the graph. Here, $t2=t1+\Delta t$. The phase difference $\Delta \varphi$ is defined as the phase difference $\Delta \varphi(t1)$ at the time point t1. More generally, the phase difference $\Delta \varphi$ may be defined as the phase difference at any time point between the two time points t1 and t2 (including t1 and t2). By executing such processing for each of a plurality of time points set in advance, the time-dependent change in the phase difference at the concerning pixel can be obtained.

A phase image is formed by representing, as an image, the values of the phase differences at time points for pixels. Such imaging processing can be realized by representing the values of the phase differences with colors or brightness. It is possible to differentiate the color indicating that the phase has increased with the lapse of time and the color indicating that the phase has decreased. For example, red is assigned to the former case while blue is assigned to the latter case. It is also possible to represent the magnitude of the phase change amount with the density of display color. With such representation methods, the direction and/or magnitude of blood flow can be represented with colors and/or density. The processing described here is applied to each pixel to form a phase image.

The time interval Δt described above can be set sufficiently small to secure phase correlation. This allows to obtain the time-dependent change in phase difference. Here, oversampling is executed in which the time interval Δt is set to be a value smaller than the period corresponding to the resolution of cross sectional images in the scan with the measurement light LS.

(Data Processor 230)

The data processor 230 executes various kinds of data processing. For example, the data processor 230 applies image processing, analysis processing, or the like to images formed by the image former 220. Specific examples thereof include various kinds of correction processing such as brightness correction and dispersion correction. In addition, the data processor 230 applies image processing, analysis processing, or the like to images acquired by the fundus camera unit 2 (e.g., fundus images, anterior segment images).

The data processor 230 includes the blood vessel region specifier 231, the gradient calculator 232, and the blood flow information generator 233. The gradient calculator 232 includes the first calculator 232a and the second calculator 232b. The blood flow information generator 233 includes the blood flow velocity calculator 2331, the blood vessel diameter calculator 2332, and the blood flow amount calculator 2333. In addition, the image processor 230 includes the cross section setter 234.

(Blood Vessel Region Specifier 231)

The blood vessel region specifier 231 specifies a blood vessel region corresponding to the interested blood vessel Db in the cross sectional image formed by the cross sectional image former 221. In addition, the blood vessel region specifier 231 specifies a blood vessel region corresponding to the interested blood vessel Db in the phase image formed by the phase image former 222. The specification of the blood vessel region is executed by analyzing the pixel values of each image (for example, threshold processing). For the phase image, for example, the blood vessel region specifier 231 may specify the blood vessel region in the phase image with reference to the blood vessel region in the cross sectional image of the interested cross section C2.

(Gradient Calculator 232)

The gradient calculator 232 calculates the gradient of the interested blood vessel Db at the interested cross section C2 based on the data acquired through the first scan. At this time, it is also possible to further use the data acquired through the second scan. The gradient calculator 232 calculates the gradient of the interested blood vessel Db at the interested cross section C2 based on the specification results of the blood vessel region and the cross section interval, for example. In the example shown in FIG. 5, the cross section interval may include the distance between the supplementary cross section C11 and the supplementary cross section C12, and the distance between the supplementary cross section C13 and the supplementary cross section C14. The cross section interval may further include the distance between the interested cross section C2 and the supplementary cross section C12, and the distance between the interested cross section C2 and the supplementary cross section C13. As described above, the gradient calculator 232 includes the first calculator 232a and the second calculator 232b.

(First Calculator 232a)

The first calculator 232a determines the first gradient of the interested blood vessel by analyzing the first data group consisting of two or more pieces of data among four or more pieces of data (i.e., cross sectional images) corresponding to the four or more supplementary cross sections acquired through the first scan. In addition, the first calculator 232a determines the second gradient of the interested blood vessel by analyzing the second data group consisting of two or more pieces of data including one or more pieces of data that are not included in the first data group.

A specific example will be described. As in the example shown in FIG. 5, a series of scans of the four supplementary cross sections C11 to C14 are executed one or more times in the first scan when the four supplementary cross sections C11 to C14 are employed. Every time the series of scans is executed, four cross sectional images (referred to as a cross sectional image group) corresponding to the four supplementary cross sections C11 to C14 are formed.

Figure 6:
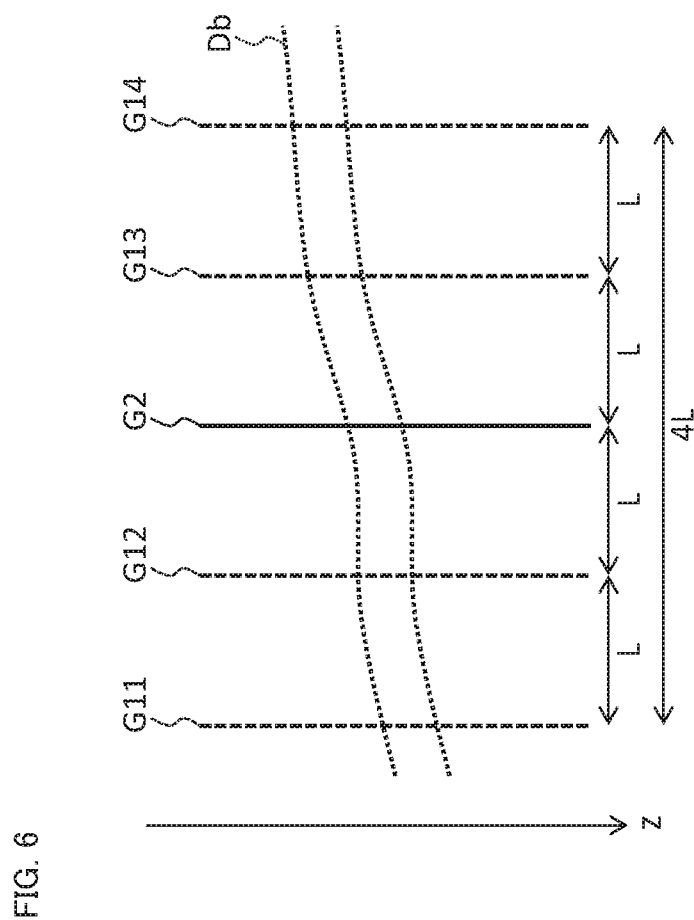
FIG. 6 is a schematic diagram for describing an example of the operation of the blood flow measurement device according to the embodiment.

FIG. 6 shows an outline of the cross sectional image group formed by such a series of scans. The four reference symbols G11 to G14 represent cross sectional images acquired through the series of scans of the four supplementary cross sections C11 to C14, respectively. The reference symbol G2 is a cross sectional image representing the interested cross section C2 acquired through the second scan executed together with the first scan. In each of the cross sectional images G11 to G14 and G2, a cross section of the interested blood vessel Db is depicted. In FIG. 6, the z coordinate axis is oriented downward, and substantially coincides with the projection direction of the measurement light LS (i.e., with the optical axis of the optical path of the measurement light LS).

The interval between adjacent cross sectional images (i.e., cross sections) is represented by L. In the present example, the two cross sectional images G11 and G12 (i.e., the supplementary cross sections C11 and C12) are disposed on one side with respect to the cross sectional image G2 (i.e., the interested cross section C2), and the two cross sectional images G13 and G14 ((i.e., the supplementary cross sections C13 and C14) are disposed on the other side. Therefore, the distance between the cross sectional images G11 and G14 at both ends (i.e., the supplementary cross sections C11 and C14 at both ends) (i.e., cross section overall width) is 4L. As described above, the cross section interval L may be any value within the range of 50 μm to 100 μm, and the cross section overall width 4L may be any value within the range of 200 μm to 400 μm.

In the present example, the two cross sectional images G11 and G14 on the outer side can be set as the first data group, and the two cross sectional images G12 and G13 on the inner side can be set as the second data group. In this case, the first calculator 232a determines the first gradient of the interested blood vessel Db by analyzing the cross sectional images G11 and G14. In addition, the first calculator 232a determines the second gradient of the interested blood vessel Db by analyzing the cross sectional images G12 and G13. That is, in the present example, the four cross sectional images G11 to G14 are divided into two mutually exclusive groups, and each of the groups is used to calculate a value of the gradient of the interested blood vessel Db. In other example, the four or more pieces of data acquired through the first scan may be divided into three or more groups, and/or may be divided into two or more groups in which a part of one group is the same as a part of another group.

Figure 7:
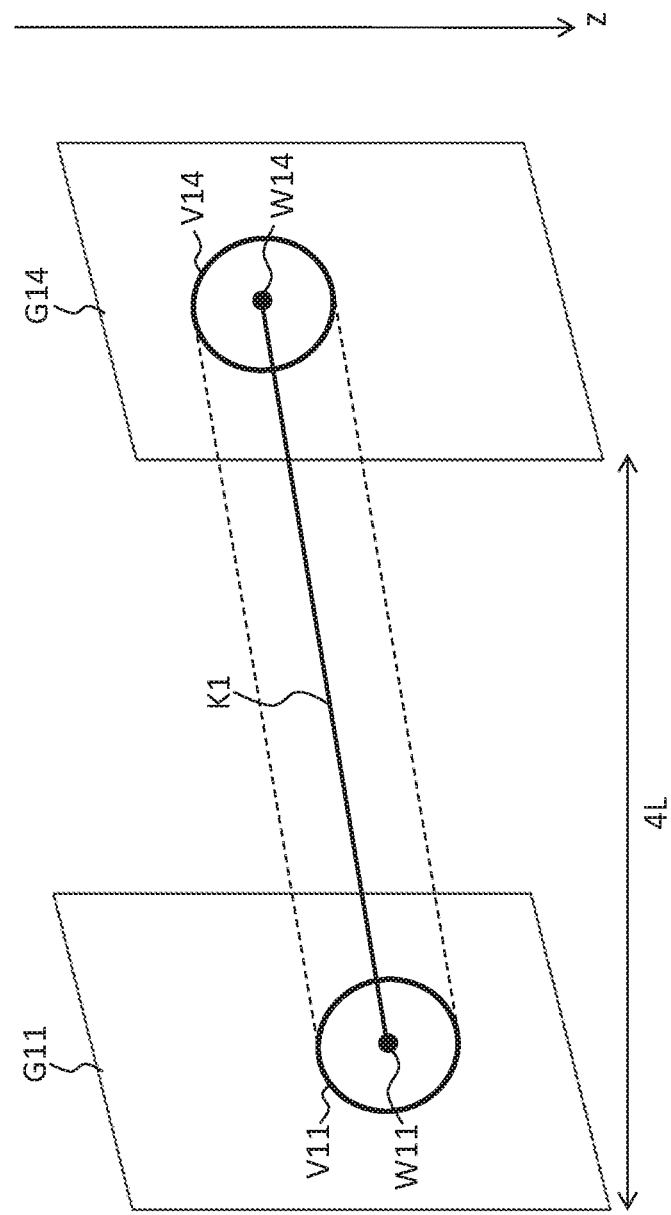
FIG. 7 is a schematic diagram for describing an example of the operation of the blood flow measurement device according to the embodiment.

An example of the gradient calculation process executed by the first calculator 232a will be described with referring to FIG. 7. In FIG. 7, the two outer cross sectional images G11 and G14 are shown. The reference symbol V11 indicates a blood vessel region in the cross sectional image G11 specified by the blood vessel region specifier 231. Similarly, the reference symbol V14 indicates a blood vessel region in the cross sectional image G14 specified by the blood vessel region specifier 231. These blood vessel regions V11 and V14 correspond to cross sections of the interested blood vessel Db. The distance between these cross sectional images G11 and G14 is the cross section overall width 4L.

The first calculator 232a calculates the first gradient of the interested blood vessel Db based on the positional relationship between the two blood vessel regions V11 and V14. The positional relationship between the two blood vessel regions V11 and V14 is obtained, for example, by connecting the two blood vessel regions V11 and V14. Specifically, the first calculator 232a specifies the representative point W11 in the blood vessel region V11 and the representative point W14 in the blood vessel region V14, and determines the line segment K1 that connects the representative points W11 and W14. The representative points W11 and W14 may be the center, the center of gravity, the highest position (i.e., the position corresponding to the smallest z coordinate value), the lowest position (i.e., the position corresponding to the largest z coordinate value), or the like. Note that the two representative points are connected by the line segment (i.e., a straight line) in the present example, but examples are not limited to the line segment. For example, when connecting representative points in three or more cross sectional images, three or more representative points can be connected by an approximate curve (e.g., a spline curve, a Bezier curve, etc.) or a polygonal line.

Further, the first calculator 232a calculates the first gradient of the interested blood vessel Db based on the line segment K1 that connects these representative points W11 and W14. For example, the first gradient is defined as an angle formed by the line segment K1 with respect to the z coordinate axis or as an angle formed by the line segment K1 with respect to a plane orthogonal to the z coordinate axis (i.e., with respect to the xy plane). In another example, when the positional relationship of the blood vessel regions is expressed by an approximate curve, a gradient at an arbitrary position on the approximate curve (for example, the gradient at the interested cross section C2) may be calculated. In still another example, when the positional relationship of the blood vessel regions is expressed by a polygonal line, a statistic (e.g., the mean value, the median, the mode, etc.) of gradients of two or more line segments included in the polygonal line can be calculated. Note that the cross section interval L is used to embed the cross sectional images G11, G14, and the like in the xyz coordinate system in the process of determining a line segment of an approximate curve.

The above example determines the gradient of the interested blood vessel Db based on the blood vessel regions; however, the gradient can also be estimated based on a predetermined region in the cross sectional image. For example, it is possible to specify a region corresponding to a predetermined tissue (e.g., the inner limiting membrane (ILM) etc.) of the fundus Ef, or a region having characteristic brightness or shape, and estimate the gradient based on the positional relationship of the regions specified from two or more cross sectional images.

The process of calculating the second gradient of the interested blood vessel Db on the basis of the two inner cross sectional images G12 and G13 is executed in the same manner as described above. The distance between the cross sectional images G12 and G13 is 2L, which is narrower than the cross section overall width. In addition, the middle position between the cross sectional image G11 and the cross sectional image G14 is the interested cross section C2, and the middle position between the cross sectional image G12 and the cross sectional image G13 is also the interested cross section C2.

(Second Calculator 232b)

Figure 8:
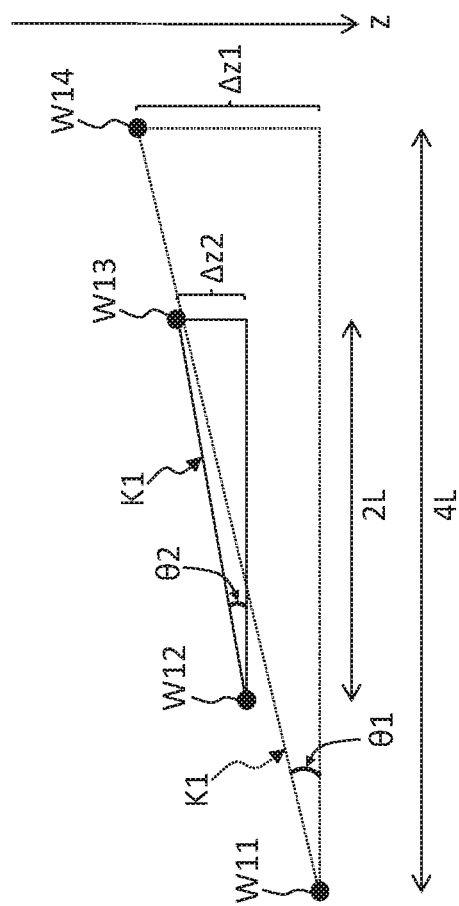
FIG. 8 is a schematic diagram for describing an example of the operation of the blood flow measurement device according to the embodiment.

The second calculator 232b determines the gradient of the interested blood vessel Db at the interested cross section C2 based on the first gradient and the second gradient determined by the first calculator 232a. FIG. 8 shows an example of the first gradient and an example of the second gradient. The reference symbols W11 to W14 indicate representative points in the cross sectional images G11 to G14 shown in FIG. 6, respectively. The reference symbols K1 indicates the line segment connecting the two outer representative points W11 and W14. The reference symbol K2 indicates the line segment connecting the two inner representative points W12 and W13. In addition, the distance between the two outer representative points W11 and W14 is 4L, and the distance between the two inner representative points W12 and W13 is 2L.

When gradient is defined with reference to the xy plane orthogonal to the z coordinate axis, the first gradient $\theta 1$ is given by $\theta 1 = \tan^{-1}(\Delta z1/4L)$, and the second gradient $\theta 2$ is given by $\theta 2 = \tan^{-1}(\Delta z2/2L)$. Here, $\Delta z1$ represents the displacement in the z direction (i.e., the difference in z coordinate values) between the two outer representative points W11 and W14, and $\Delta z2$ represents the displacement in the z direction (i.e., the difference in z coordinate values) between the two inner representative points W12 and W13. Note that there is a relationship of $\varphi i = 90° - \theta i$ between the gradient $\theta i$ that has the xy plane orthogonal to the z coordinate axis as a reference and the gradient $\varphi i$ that has the z coordinate axis as a reference. The gradient $\theta i$ and the gradient $\varphi i$ are equivalent since if one is determined, the other is also determined in a unique manner.

The first example of the process executed by the second calculator 232b will be described with referring to FIG. 8. The second calculator 232b first sets an allowable range based on the second gradient $\theta 2$. This allowable range is set on the basis of, for example, an error a and the second gradient $\theta 2$. Here, the error a is set in advance on the basis of the cross section overall width 4L, the cross section interval L, and/or the number of cross sections. The second calculator 232b determines whether or not the first gradient $\theta 1$ satisfies the following relation: $\theta 2 - \alpha < \theta 1 < \theta 2 + \alpha$. That is, the second calculator 232b determines whether or not the first gradient $\theta 1$ is included within the range of the error a with respect to the second gradient $\theta 2$. This is to evaluate the meandering state of the interested blood vessel Db between the supplementary cross sections C11 and C14 at both ends with the second gradient $\theta 2$, and to determine whether or not the first gradient $\theta 1$ is included within the allowable error range corresponding to it.

When the first gradient $\theta 1$ is included in the allowable range, the first gradient $\theta 1$ is adopted as the gradient $\theta$ of the interested blood vessel Db at the interested cross section C2. On the other hand, when the first gradient θ1 is not included in the allowable range, the first gradient θ1 can be ignored and the subsequent processing can be executed. Alternatively, the second gradient may be adopted.

The second example of the process executed by the second calculator 232b will be described. The second calculator 232b calculates a statistic of the first gradient θ1 and the second gradient θ2. This statistic is, for example, the mean value (i.e., the simple mean, a weighted mean, etc.). The calculated statistic is adopted as the gradient θ of the interested blood vessel Db at the interested cross section C2.

(Blood Flow Information Generator 233)

The blood flow information generator 233 generates blood flow information on the subject's eye E based on the data acquired through scanning the interested cross section with the second scan and on the gradient θ determined by the second calculator 232b. More specifically, the blood flow information generator 233 generates blood flow information on the interested blood vessel Db based on the phase image acquired by Doppler OCT technique and on the gradient θ of the interested blood vessel Db at the interested cross section C2 calculated by the second calculator 232b. As mentioned above, the blood flow information generator 233 includes the blood flow velocity calculator 2331, the blood vessel diameter calculator 2332, and the blood flow amount calculator 2333.

(Blood Flow Velocity Calculator 2331)

Based on the time-dependent change in the phase difference obtained as the phase image, the blood flow velocity calculator 2331 calculates the blood flow velocity at the interested cross section C2 for the blood flowing through the interested blood vessel Db. The parameter to be calculated may be the blood flow velocity at a certain time point or may be the time-dependent change in the blood flow velocity. The time-dependent change in the blood flow velocity is referred to as blood flow velocity variation information. When the blood flow velocity at a certain time point is determined, the blood flow velocity at a predetermined time phase in an electro cardiogram (e.g., time phase corresponding to the R wave) may be selectively acquired. When the time-dependent change in the blood flow velocity is determined, the measurement period is the whole or an arbitrary part of the period taken for the scan of the interested cross section C2.

When the blood flow velocity variation information is acquired, the blood flow velocity calculator 2331 can further calculate a statistic of the blood flow velocity in the measurement period. Examples of the statistic include the mean value, the standard deviation, the variance, the median, the global maximum, the global minimum, the local maximum, and the local minimum. The blood flow velocity calculator 2331 can also create a histogram on the blood flow velocity values.

The blood flow velocity calculator 2331 calculates the blood flow velocity using Doppler OCT technique as described above. In the blood flow velocity calculation, the gradient θ of the interested blood vessel Db at the interested cross section C2 calculated by the gradient calculator 232 is taken into account. Specifically, the gradient calculator 232 applies the following formula to the blood flow velocity calculation.

(Formula 1)

$$\Delta f = \frac{2nv\cos\theta}{\lambda} \quad (1)$$

Here:
Δf indicates the Doppler shift given to the scattered light of the measurement light LS;
n indicates the refractive index of the medium (i.e., blood);
v indicates the flow velocity of the medium (i.e., blood flow velocity);
θ indicates the angle between the incident direction of the measurement light LS and the flow direction (i.e., gradient) of the medium; and
λ indicates the center wavelength of the measurement light LS.

In the present embodiment, n and λ are known, Δf is obtained from the time-dependent change in the phase difference, and θ is the gradient or is determined from the gradient. The blood flow velocity v is calculated by substituting these values into the formula (1).

(Blood Vessel Diameter Calculator 2332)

The blood vessel diameter calculator 2332 calculates the diameter of the interested blood vessel Db at the interested cross section C2. Examples of this calculation include the first calculation method that utilizes a fundus image and the second calculation method that utilizes a cross sectional image.

When applying the first calculation method, an area of the fundus Ef including the location of the interested cross section C2 is photographed in advance. The fundus image thus obtained may be an observation image (e.g., a frame(s) thereof), or may be a photographed image. When the photographed image is a color image, any image obtained from the color image (e.g., a red-free image) may be used.

The blood vessel diameter calculator 2332 sets a scale of the fundus image based on various kinds of factors that determine the relationship between the scale of the image and the scale in the real space such as the photographing angle of view (i.e., the photographing magnification), the working distance, the information on the eyeball optical system. The scale of the fundus image may represent length in the real space. As a specific example, the scale associates the interval between adjacent pixels with the scale in the real space (e.g., the pixel interval is equal to 10 μm). It is possible to determine, in advance, the relationship between various values of the above factors and the scale in the real space, and to store information in the form of a table or a graph that represents the determined relationship. In this case, the blood vessel diameter calculator 2332 selects and applies the scale corresponding to the above factors.

Based on the scale and the pixels included in the blood vessel region in the cross sectional image G2, the blood vessel diameter calculator 2332 calculates the diameter of the interested blood vessel Db at the interested cross section C2, that is, calculates the diameter of the blood vessel region. As a specific example, the blood vessel diameter calculator 2332 may calculate the maximum or the mean value of a plurality of diameters of the blood vessel region corresponding to different directions. The blood vessel diameter calculator 2332 may determine an approximate circle or an approximate ellipse of the contour of the blood vessel region and calculate the diameter of the approximate circle or the approximate ellipse. Note that once the blood vessel diameter of the blood vessel region is determined, the area (i.e., the square measure) of the blood vessel region can (substantially) be calculated. Hence, the area can be calculated in place of the blood vessel diameter.

Figure 5:
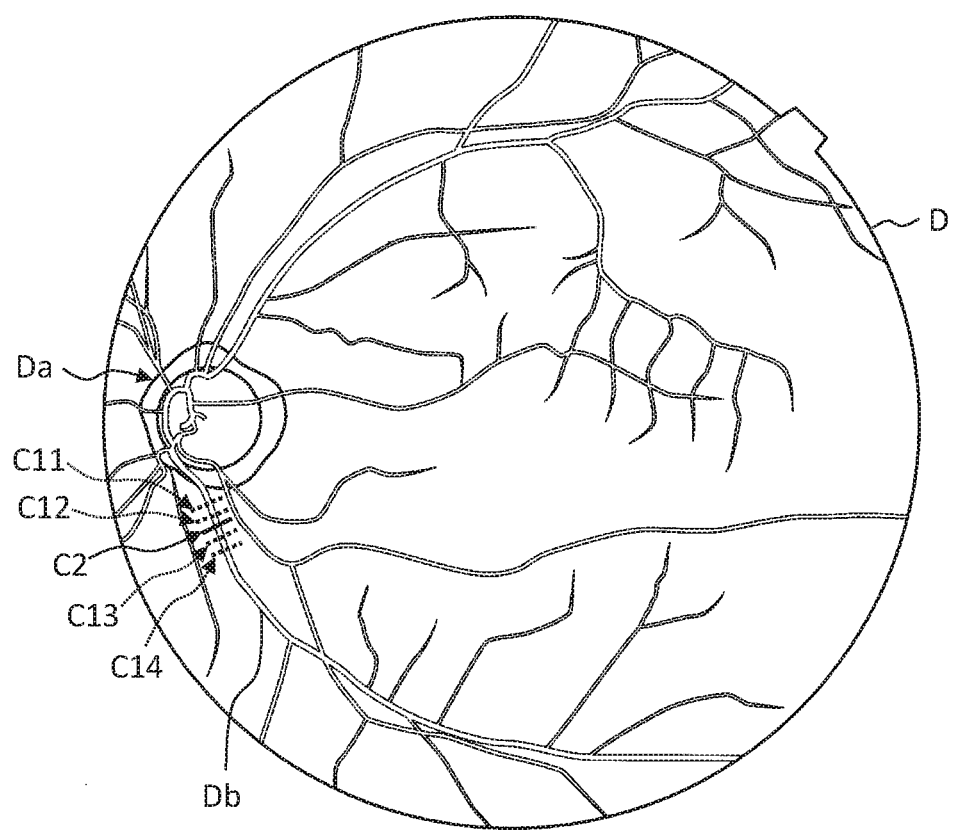
FIG. 5 is a schematic diagram for describing an example of the operation of the blood flow measurement device according to the embodiment.

The second calculation method will be described. In the second calculation method, a cross sectional image of the fundus Ef at the interested cross section C2 is used. The cross sectional image may be a cross sectional image obtained based on the second scan or a cross sectional image obtained using a different method. The scale of the cross sectional image is determined according to the scan mode of the measurement light LS. When scanning the interested cross section C2 as shown in FIG. 5, the length of the interested cross section C2 is determined based on various kinds of factors that determine the relationship between the scale of the image and the scale in the real space such as the working distance, the information on the eyeball optical system. The blood vessel diameter calculator 2332, for example, determines the interval between adjacent pixels based on the length of the interested cross section C2, and calculates the diameter of the interested blood vessel Db at the interested cross section C2 in the same manner as in the first calculation method.

(Blood Flow Amount Calculator 2333)

Based on the calculation result of the blood flow velocity and the calculation result of the blood vessel diameter, the blood flow amount calculator 2333 calculates the flow amount (or, flow volume or flow rate) of the blood that flows through the interested blood vessel Db. An example of the calculation process will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is given by the following formula.

(Formula 2)

$$Q = \frac{\pi w^2}{8} Vm \qquad (2)$$

The blood flow amount calculator 2333 substitutes the blood vessel diameter w calculated by the blood vessel diameter calculator 2332 and the maximum blood flow velocity Vm based on the blood flow velocity calculated by the blood flow velocity calculator 2331 into the formula (2) to determine the blood flow amount Q.

(Cross Section Setter 234)

The main controller 211 displays a fundus image on the display device 241. The fundus image may be an observation image or a photographed image. The fundus image may be any image that constitutes a photographed image. The user operates the operation device 242 to designate the interested cross section C2 in the displayed fundus image. Based on the designated interested cross section C2 and the fundus image, the cross section setter 234 sets four (or more) supplementary cross sections C11 to C14 to which the first scan is to be applied. As mentioned above, the interested cross section C2 is designated in such a manner that the interested cross section C2 intersects the desired interested blood vessel Db.

For example, a pointing device is used to perform the operation of designating the interested cross section C2 in the fundus image. When the display device 241 includes a touch panel, the user touches a desired location in the displayed fundus image to designate the interested cross section C2. In this case, parameters (e.g., orientation, length) of the interested cross section C2 is set manually or automatically.

When setting manually, for example, the user can use a predetermined interface to set the parameters. The interface may include hardware such as a switch or may include software such as a graphical user interface (GUI).

When setting automatically, for example, the cross section setter 234 sets the parameters based on the location designated in the fundus image by the user. A predetermined value of the length may be automatically set. Alternatively, the length may be automatically set based on the designated location and locations of blood vessels near the designated location. The predetermined value of the length is designated, for example, based on typical distance between a predetermined interested blood vessel and blood vessels in the vicinity thereof. Information on the typical distance may be generated based on clinical data. This is the same in the case in which the designated location and the locations of the nearby blood vessels are taken into account.

When automatically setting the orientation of the interested cross section C2, a predetermined orientation may be set, or the orientation of the interested blood vessel Db may be taken into account. In the former case, information representing the orientation of a predetermined interested blood vessel at a plurality of locations is generated in advance, and the information is referred to. The information may be generated based on clinical data. In the latter case, the running direction of the interested blood vessel Db at the designated location is determined, and the orientation of the interested cross section C2 is set based on the designated running direction. The process of designating the running direction is performed through thinning of the interested blood vessel Db, for example. In either case, the orientation of the interested cross section C2 may be set in such a manner that the interested cross section C2 orthogonally intersects the running direction in the xy plane.

Next, the process of setting the supplementary cross sections C11 to C14 to which the first scan is to be applied will be described. The cross section setter 234 sets the supplementary cross sections C11 to C14 at locations that are predetermined distances away from the interested cross section C2. The predetermined distances correspond to the cross section interval (L) and the cross section overall width (4L) mentioned above. Further, the length and/or the orientation of the supplementary cross sections C11 to C14 may be set in the same way as for the interested cross section C2.

The data processor 230 having the above functions includes, for example, a processor, a RAM, a ROM, a hard disk drive, a circuit board, and the like. Computer programs for the processor to execute the above functions are stored in advance in the storage device such as the hard disk drive.

(User Interface 240)

The user interface 240 includes the display device 241 and the operation device 242. The display device 241 includes a display device in the arithmetic and control unit 200, the display device 3, and the like. The operation device 242 includes an operation device in the arithmetic and control unit 200. The user interface 240 may include a device, such as a touch panel, that has a display function and an operation function.

[Operation]

Figure 9:
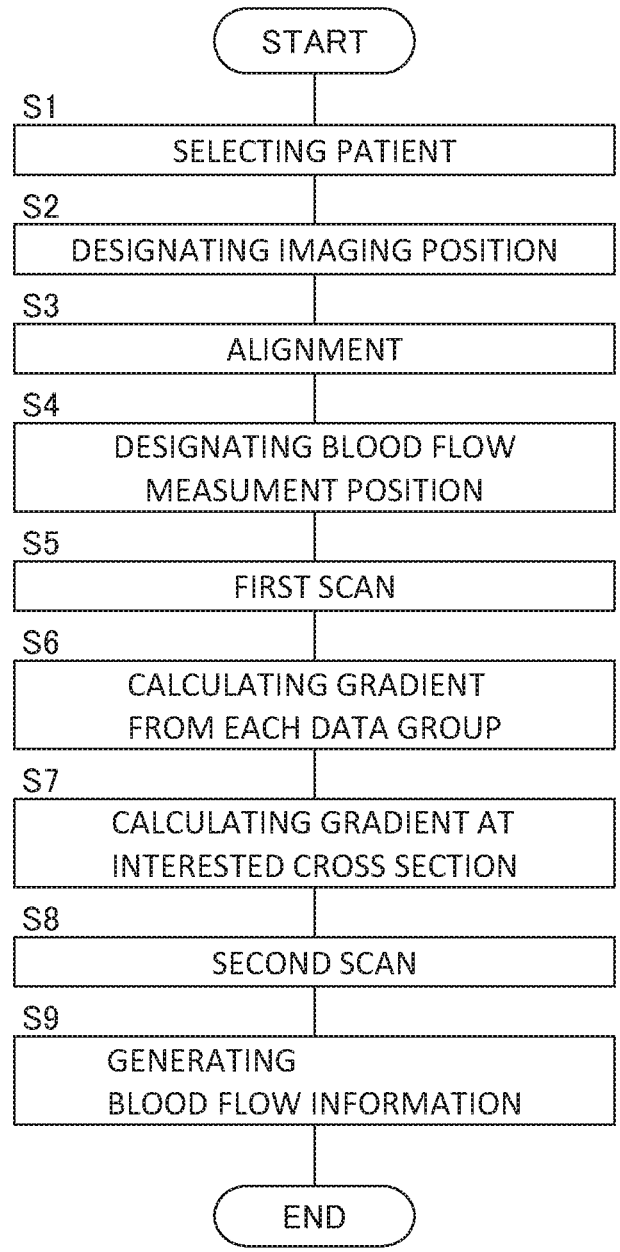
FIG. 9 is a flow chart illustrating an example of the operation of the blood flow measurement device according to the embodiment.

The operation of the blood flow measurement device 1 will be described. FIG. 9 shows an example of the operation of the blood flow measurement device 1.

(S1: Selecting Patient)

First, a patient to be subjected to blood flow measurement is selected. The patient selection is performed, for example, by inputting a patient ID.

(S2: Designating Imaging Position)

The user designates a position to perform imaging of the subject's eye E, for example, by adjusting the position of the optical system of the blood flow measurement device 1.

(S3: Alignment)

Next, the position adjustment (i.e., alignment) of the optical system with respect to the subject's eye E is performed. The alignment is performed, for example, by using the alignment indicator. Alternatively, in the case where two or more anterior segment cameras, disclosed in Japanese Unexamined Patent Application Publication No. 2013-248376 by the present applicant, are provided, the alignment can be performed based on two or more images obtained by photographing the anterior eye segment substantially simultaneously from different directions. In the present step, the focus adjustment etc. may also be performed.

(S4: Designating Blood Flow Measurement Position)

Subsequently, the position where the blood flow measurement to be performed (in particular, the interested cross section C2) is designated. At this time, a process for determining whether or not the cross section designated by the user is appropriate may be executed. An example of the appropriateness determination includes: a process of calculating the gradient of the designated blood vessel at the designated cross section based on images of the designated cross section and the vicinity thereof acquired through OCT scan; and a process of determining whether or not the calculated gradient falls within an allowable range. When the calculated gradient is included in the predetermined allowable range, the designated cross section is adopted as a cross section at which blood flow is to be measured (i.e., adopted as the interested cross section C2). When the interested cross section C2 has been determined, the cross section setter 234 sets four (or more) supplementary cross sections C11 to C14 to which the first scan is to be applied.

(S5: First Scan)

The blood flow measurement device 1 applies OCT scans to the supplementary cross sections C11 to C14 set by the cross section setter 234 in step S4 (that is, the blood flow measurement device 1 executes the first scan). The OCT scans performed in the first scan is executed in the following order, for example.

In the first example of the scan sequence, the OCT scans of the four supplementary cross sections C11 to C14 is performed in the following order: "C11→C14→C12→C13". This corresponds to the series of scans described above. In other words, the first example performs: successive scans on the supplementary cross sections C11 and C14 corresponding to the first data group (e.g., the two outer cross sectional images G11 and G14); and successive scans on the supplementary cross sections C12 and C13 corresponding to the second data group (e.g., the two inner cross sectional images G12 and G13). A purpose of the first example thus performed is to shorten the time interval between two (or more) OCT scans for acquiring two (or more) data included in the first data group, thereby reducing the influence of the movement of the subject's eye E during the OCT scans. According to the first example, a single cross sectional image is formed for each of the four supplementary cross sections C11 to C14.

In the second example of the scan sequence, the blood flow measurement device 1 repeatedly executes the series of scans "C11→C14→C12→C13" in the first example. To be more specific, the blood flow measurement device 1, in the second example, executes OCT scans of the four supplementary cross sections C11 to C14 in the following order: "C11→C14→C12→C13→C11→C14→C12→C13→C11 ...". In other words, in the second example, as in the first example, the supplementary cross sections C11 and C14 corresponding to the first data group (e.g., the two outer cross sectional images G11 and G14) are successively scanned, and the supplementary cross sections C12 and C13 corresponding to the second data group (e.g., the two inner cross sectional images G12 and G13) are successively scanned. In addition to such a sequence, the blood flow measurement device 1 executes the scans of the supplementary cross sections C11 and C14 corresponding to the first data group, and the scans of the supplementary cross sections C12 and C13 corresponding to the second data group, in an alternate manner. According to the second example, N cross sectional images are formed for each of the four supplementary cross sections C11 to C14. Here, N represents the number of repetitions of the series of scans.

In the first example and the second example, two data groups are created from the data acquired through the first scan. On the other hand, the data acquired through the first scan may be used for creating three or more data groups. For example, when creating three data groups from the data acquired through the first scan, similarly to the first example, the supplementary cross section group corresponding to the first data group can be successively scanned, the supplementary cross section group corresponding to the second data group can be successively scanned, and the supplementary cross section group corresponding to the third data group can be successively scanned. In addition, similarly to the second example, the scans on the supplementary cross section group corresponding to the first data group, the scans on the supplementary cross section group corresponding to the second data group, and the scans on the supplementary cross section group corresponding to the third data group can be executed in a cyclic manner. The same applies to a case where four or more data groups are created from the data acquired through the first scan. In the present embodiment, "alternative execution" includes such "cyclic execution".

(S6: Calculating Gradient θi from Each Data Group)

The first calculator 232a determines the first gradient θ1 of the interested blood vessel Db by analyzing the first data group acquired in step S5. In addition, the first calculator 232a determines the second gradient θ2 of the interested blood vessel Db by analyzing the second data group.

In the case where the first example of the scan sequence is employed in step S5, the first calculator 232a calculates the first gradient θ1 based on the two outer cross sectional images G11 and G14, and calculates the second gradient θ2 based on the two inner cross sectional images G12 and G13 (see FIG. 8).

Alternatively, in the case where the second example of the scan sequence is employed in step S5, based on the total number 4 N of cross sectional images formed by N for each of the four supplementary cross sections C11 to C14, the blood flow measurement device 1 calculates a plurality of values for the gradient of the interested blood vessel Db. The combination of the 4 N cross sectional images for obtaining this plurality of values is arbitrary. A specific example will be described later.

(S7: Calculating Gradient θ at Interested Cross Section)

Based on the first gradient θ1 and the second gradient θ2 obtained in step S6, the second calculator 232b determines the gradient θ of the interested blood vessel Db at the interested cross section C2. It should be noted that steps S6 and S7 may be executed after the second scan in step S8.

(S8: Second Scan)

The blood flow measurement device 1 executes a repetitive OCT scan of the interested cross section C2 designated in step S4 (that is, the blood flow measurement device 1 executes the second scan). Based on the data acquired through the second scan, the phase image former 222 forms a phase image representing the time-dependent change in the phase difference at the interested cross section C2. In addition, the cross sectional image former 221 forms the cross sectional image G2 of the interested cross section C2 based on the same data. The data processor 230 (e.g., the blood vessel region specifier 231, the blood vessel diameter calculator 2332, etc.) determines the diameter of the interested blood vessel Db at the interested cross section C2.

(S9: Generating Blood Flow Information)

The blood flow velocity calculator 2331 calculates the blood flow velocity at the interested cross section C2 based on the gradient θ calculated in step S7 and the phase image acquired in step S8. In addition, the blood flow amount calculator 2333 calculates the flow amount of the blood flowing through the interested blood vessel Db based on the calculation result of the blood flow velocity and the calculation result of the blood vessel diameter obtained in step S8.

The main controller 211 controls the display device 241 to display blood flow information including the calculation result of the blood flow velocity, the calculation result of the blood flow amount, and the like. Further, the main controller 211 associates the blood flow information with the patient ID inputted in step S1 and stores the blood flow information in the storage 212. This terminates the processing relating to the blood flow measurement in the present example.

A specific example in the case where the second example of the scan sequence is employed in the first scan in step S5 will be described.

It is assumed that the number N of repetitions of the series of scans "C11→C14→C12→C13" for the four supplementary cross sections C11 to C14 is equal to 4 (that is, N=4). Four cross sectional images obtained from the n-th series of scans are described as the followings (n=1 to 4): the cross sectional image G11($n$) corresponding to the supplementary cross section C11; the cross sectional image G12($n$) corresponding to the supplementary cross section C12; the cross sectional image G13($n$) corresponding to the supplementary cross section C13; and the cross sectional image G14($n$) corresponding to the supplementary cross section C14.

FIG. 10 shows an example of an aspect of combination of these 16 cross sectional images for calculating the gradient of the interested blood vessel Db. The combination aspect shown in FIG. 10 includes the seven combinations (#1, #2, . . . , #7).

The first combination #1 includes the four cross sectional images G11(1), G12(1), G13(1) and G14(1) acquired through the first series of scans. The first calculator 232$a$ calculates the first gradient θ1(1) based on the cross sectional images G11(1) and G14(1), and calculates the second gradient θ2(1) based on the cross sectional images G12(1) and G13(1). Further, the second calculator 232$b$ determines the gradient θ(1) of the interested blood vessel Db at the interested cross section C2 based on the first gradient θ1(1) and the second gradient θ2(1).

The second combination #2 includes two cross sectional images G11(2) and G12(2) acquired through the second series of scans, and two cross sectional images G13(1) and G14(1) acquired through the first series of scans. The first calculator 232$a$ calculates the first gradient θ1(2) based on the cross sectional images G11(2) and G14(1), and calculates the second gradient θ2(2) based on the cross sectional images G12(2) and G13(1). Further, the second calculator 232$b$ determines the gradient θ(2) of the interested blood vessel Db at the interested cross section C2 based on the first gradient θ1(2) and the second gradient θ2(2).

Likewise, the gradient θ(3) to the gradient θ(7) of the interested blood vessel Db at the interested cross section C2 can be calculated for the third to seventh combinations #3 to #7, respectively.

Based on the seven gradients θ (1) to θ (7) thus acquired, the second calculator 232$b$ calculates the final result θ of the gradient of the interested blood vessel Db at the interested cross section C2. This process may include, for example, a process of calculating a statistic (e.g., the simple mean, a weighted mean, the median, the mode, etc.) of the seven gradients θ(1) to θ(7). Alternatively, the process may include a process of determining n=n0 for which the difference between the first gradient θ1($n$) and the second gradient θ2($n$) becomes minimum, and a process of adopting the first gradient θ1($n$0), the second gradient θ2($n$0) or θ($n$0) obtained from them.

Actions and Effects

Actions and effects of the blood flow measurement device according to the present embodiment will be described.

A blood flow measurement device of the embodiment is configured to generate blood flow information based on data collected by repeatedly scanning an interested cross section (C2) intersecting a blood vessel (the interested blood vessel Db) of an eye fundus using OCT. The blood flow measurement device includes a data collector, a first calculator, a second calculator, and a blood flow information generator. The data collector collects data (the cross sectional images G11 to G14, etc.) by scanning four or more cross sections (the supplementary cross sections C11 to C14, etc.) intersecting the blood vessel using OCT. The first calculator determines a first gradient (θ1) of the blood vessel by analyzing a first data group (the cross sectional images G11 and G14, etc.) consisting of two or more pieces of data among the four or more pieces of data (the cross sectional images G11 to G14, etc.) collected by the data collector. In addition, the first calculator determines a second gradient (θ2) of the blood vessel by analyzing a second data group (the cross sectional images G12 and G13, etc.) consisting of two or more pieces of data including one or more pieces of data that is not included in the first data group. The second calculator determines a gradient (θ) of the blood vessel at the interested cross section based on the first gradient and the second gradient determined by the first calculator. The blood flow information generator generates the blood flow information based on the gradient determined by the second calculator and the data (the phase image, etc.) collected by repeatedly scanning the interested cross section. In the above embodiment, which is merely an example, the data collector includes the optical system for OCT and the image former 220. The first calculator includes the first calculator 232$a$, and the second calculator includes the second calculator 232$b$. In addition, the blood flow information generator includes at least part of the blood flow information generator 233.

According to such an embodiment, the gradient of the interested blood vessel can be estimated twice or more times by changing the combination of the data obtained by performing OCT scans on the four or more supplementary cross sections. In addition, on the basis of these estimated values, the blood flow measurement device 1 can determine the gradient of the interested blood vessel at the interested cross section for Doppler OCT. Here, the distance between supplementary cross sections located at both ends among the four or more supplementary cross sections (the cross section overall width) is set wider than that in the conventional way to secure the accuracy and the precision of calculation. For example, the distance may be set to 400 μm while that of the conventional way is 200 μm. Further, the interval (cross section interval) of five or more cross sections including the supplementary cross sections and the interested cross section may be set by taking account of the influence of errors caused by meandering of the blood vessel. Furthermore, the number of supplementary cross sections can also be arbitrarily set. Therefore, it is possible to optimize the setting of the supplementary cross sections for estimating the orientation of the blood vessel.

In the embodiment, the first data group may include one or both of the supplementary cross sections located at both ends among the four or more supplementary cross sections. For example, in the above embodiment, the first data group includes the supplementary cross sections C11 and C14 located at both ends of the four supplementary cross sections C11 to C14. Note that the first data group can also be configured to include only one of the supplementary cross sections C11 and C14.

In the embodiment, the first data group and the second data group may be configured in such a manner that the distance between two cross sections located at both ends of the first data group and the distance between two cross sections located at both ends of the second data group are different from each other. For example, in the above embodiment, the first data group includes the supplementary cross sections C11 and C14 that are away from each other by the distance 4L, and the second data group includes the supplementary cross sections C12 and C13 that are away from each other by the distance 2L. With such a configuration, the blood flow measurement device 1 can determine the gradient θ1 having a relatively high accuracy and precision by using the first data group. Meanwhile, the blood flow measurement device 1 can determine the gradient θ2 having a relatively low influence of meandering of the blood vessel by using the second data group. In addition, from these gradients determined, the final gradient θ can be acquired.

In the embodiment, the data collector may successively execute scans of two or more supplementary cross sections corresponding to the first data group and successively execute scans of two or more supplementary cross sections corresponding to the second data group. As a result, the time interval between two or more OCT scans for collecting two or more pieces of data included in the first data group can be shortened, and the error caused by the movement of the subject's eye during that period can be reduced.

Further, the data collector can alternatively execute the scans of the two or more supplementary cross sections corresponding to the first data group and the scans of the two or more supplementary cross sections corresponding to the second data group. As a result, a plurality of samples (cross sectional images) for each supplementary cross section can be acquired, and it is possible to reduce errors in gradient calculation. By alternatively executing these two scans, the error caused by the movement of the subject's eye can be reduced. Note that as described above, the present embodiment also includes a case where executing scans of three or more supplementary cross section groups corresponding to three or more data groups in a cyclic manner.

The configurations described above are merely examples for implementing the present invention. Therefore, it is possible to make arbitrary modifications (omissions, replacements, additions, etc.) within the scope of the gist of the present invention.

What is claimed is:

1. A blood flow measurement device that generates blood flow information based on data collected by repeatedly scanning an interested cross section intersecting a blood vessel of an eye fundus using optical coherence tomography, the blood flow measurement device comprising:
   a data collector that collects data by scanning four or more cross sections intersecting the blood vessel using optical coherence tomography, wherein the four or more cross sections are different than the interested cross section;
   a first calculator that determines a first gradient of the blood vessel by analyzing a first data group consisting of two or more pieces of data among four or more pieces of data corresponding to the four or more cross sections collected by the data collector and that determines a second gradient of the blood vessel by analyzing a second data group consisting of two or more pieces of data including one or more pieces of data that is not included in the first data group;
   a second calculator that determines a gradient of the blood vessel at the interested cross section based on the first gradient and the second gradient determined by the first calculator; and
   a blood flow information generator that generates the blood flow information based on the gradient determined by the second calculator and the data collected by repeatedly scanning the interested cross section.

2. The blood flow measurement device of claim 1, wherein the first data group comprises one or both of a first cross section and a second cross section, the first cross section being located at one end of an arrangement of the four or more cross sections, and the second cross section being located at another end of the arrangement of the four or more cross sections.

3. The blood flow measurement device of claim 1, wherein a distance between two cross sections located at both ends of the first data group and a distance between two cross sections located at both ends of the second data group are different from each other.

4. The blood flow measurement device of claim 3, wherein
   the data collector collects data by scanning four cross sections intersecting the blood vessel,
   the first data group consists of two cross sections among the four or more cross sections, one of the two cross sections being located at one end of an arrangement of the four cross sections, and another of the two cross sections being located at another end of the arrangement of the four cross sections, and
   the second data group consists of two cross sections that are not included in the first data group.

5. The blood flow measurement device of claim 1, wherein the data collector successively executes scans of two or more cross sections corresponding to the first data group and successively executes scans of two or more cross sections corresponding to the second data group.

6. The blood flow measurement device of claim 5, wherein the data collector alternatively executes scans of the two or more cross sections corresponding to the first data group and scans of the two or more cross sections corresponding to the second data group.

7. The blood flow measurement device of claim 1, wherein five or more cross sections comprising the interested cross section and the four or more cross sections are positioned at equally spaced intervals along the blood vessel.

8. The blood flow measurement device of claim 1, wherein
a number of the four or more cross sections is an even number, and
the interested cross section is disposed at a center of an odd number of cross sections comprising the interested cross section and the four or more cross sections.

9. The blood flow measurement device of claim 1, wherein the second calculator sets an allowable range based on the second gradient and on an error value based on a cross section attribute, and the second calculator adopts the first gradient as the gradient of the blood vessel at the interested cross section when the first gradient is within the allowable range.

10. The blood flow measurement device of claim 1, wherein the second calculator calculates a statistic from the first gradient and the second gradient and adopts the statistic as the gradient of the blood vessel at the interested cross section.

11. A method of generating blood flow information comprising:
collecting data by repeatedly scanning an interested cross section intersecting a blood vessel of an eye fundus using optical coherence tomography;
collecting data by scanning four or more cross sections intersecting the blood vessel using optical coherence tomography, wherein the four or more cross sections are different than the interested cross section;
determining a first gradient of the blood vessel by analyzing a first data group consisting of two or more pieces of data among four or more pieces of data corresponding to the four or more cross sections;
determining a second gradient of the blood vessel by analyzing a second data group consisting of two or more pieces of data including one or more pieces of data that is not included in the first data group;
determining a gradient of the blood vessel at the interested cross section based on the first gradient and the second gradient; and
generating the blood flow information based on the gradient of the blood vessel at the interested cross section and the data collected by repeatedly scanning the interested cross section.

12. The method of claim 11, wherein the first data group comprises one or both of a first cross section and a second cross section among the four or more cross sections, the first cross section being located at one end of an arrangement of the four or more cross sections, and the second cross section being located at another end of the arrangement of the four or more cross sections.

13. The method of claim 11, wherein a distance between two cross sections located at both ends of the first data group and a distance between two cross sections located at both ends of the second data group are different from each other.

14. The method of claim 13, wherein
collecting data by scanning four cross sections intersecting the blood vessel,
the first data group consists of two cross sections, one of the two cross sections being located a one end of an arrangement of the four cross sections among the four or more cross sections, and another of the two cross sections being located at another end of the arrangement of the four cross sections and
the second data group consists of two cross sections that are not included in the first data group.

15. The method of claim 11, wherein
collecting data by successively executing scans of two or more cross sections corresponding to the first data group and by successively executing scans of two or more cross sections corresponding to the second data group.

16. The method of claim 15, wherein
collecting data by alternatively executing scans of the two or more cross sections corresponding to the first data group and scans of the two or more cross sections corresponding to the second data group.

17. The method of claim 11, wherein five or more cross sections comprising the interested cross section and the four or more cross sections are positioned at equally spaced intervals along the blood vessel.

18. The method of claim 11, wherein
a number of the four or more cross sections is an even number, and
the interested cross section is disposed at a center of an odd number of cross sections comprising the interested cross section and the four or more cross sections.

19. The method of claim 11, wherein
setting an allowable range based on the second gradient and on an error value based on a cross section attribute, and
adopting the first gradient as the gradient of the blood vessel at the interested cross section when the first gradient is within the allowable range.

20. The method of claim 11, wherein
calculating a statistic from the first gradient and the second gradient, and
adopting the statistic as the gradient of the blood vessel at the interested cross section.

* * * * *